United States Patent
Lin et al.

(10) Patent No.: US 6,294,074 B1
(45) Date of Patent: Sep. 25, 2001

(54) ELECTRODE DESIGN FOR CORROSION MONITORING USING ELECTROCHEMICAL NOISE MEASUREMENTS

(75) Inventors: YuPo J. Lin, Westmont; Edward J. St. Martin, Libertyville; James R. Frank, Glen Ellyn, all of IL (US); Daniel H. Pope, Bayfield, CO (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/573,575

(22) Filed: May 18, 2000

(51) Int. Cl.[7] .................................................. G01N 27/26
(52) U.S. Cl. ...................... 205/775.5; 205/777; 204/280; 204/404; 204/412
(58) Field of Search .................................. 204/404, 412, 204/280; 205/775.5, 777

(56) References Cited

U.S. PATENT DOCUMENTS

| | | | |
|---|---|---|---|
| 5,139,627 | * | 8/1992 | Eden et al. .................. 205/775.5 |
| 5,275,704 | * | 1/1994 | Yang .............................. 204/404 |
| 5,286,357 | * | 2/1994 | Smart et al. ................... 205/775.5 |
| 5,425,867 | * | 6/1995 | Dawson et al. ................ 204/404 |
| 5,888,374 | | 3/1999 | Pope et al. .................... 205/775.5 |
| 6,010,889 | * | 1/2000 | Geary et al. ................... 204/403 |
| 6,015,484 | | 1/2000 | Martinchek et al. ........... 205/775.5 |

* cited by examiner

*Primary Examiner*—Bruce F. Bell
(74) *Attorney, Agent, or Firm*—Joan Pennington

(57) ABSTRACT

An electrode design is provided for corrosion monitoring using electrochemical noise measurements. Electrochemical probes are used for sensing electrochemical noise voltage values and electrochemical noise current values. The electrochemical probes include a pair of working electrodes formed of the same material of the monitored metal pipes or storage vessels and a reference electrode formed of a corrosion resistant material. Each of the pair of working electrodes has a defined surface roughness. One of the pair of working electrodes has reduced roughness, whereby sensitivity to sustained localized pitting corrosion is increased in the working electrode with reduced roughness. By reducing the surface roughness of one of the pair of working electrodes, increased sensitivity to sustained localized pitting corrosion is provided while the current noise can be used to accurately measure the general corrosion rate on the unpolished electrode.

12 Claims, 4 Drawing Sheets

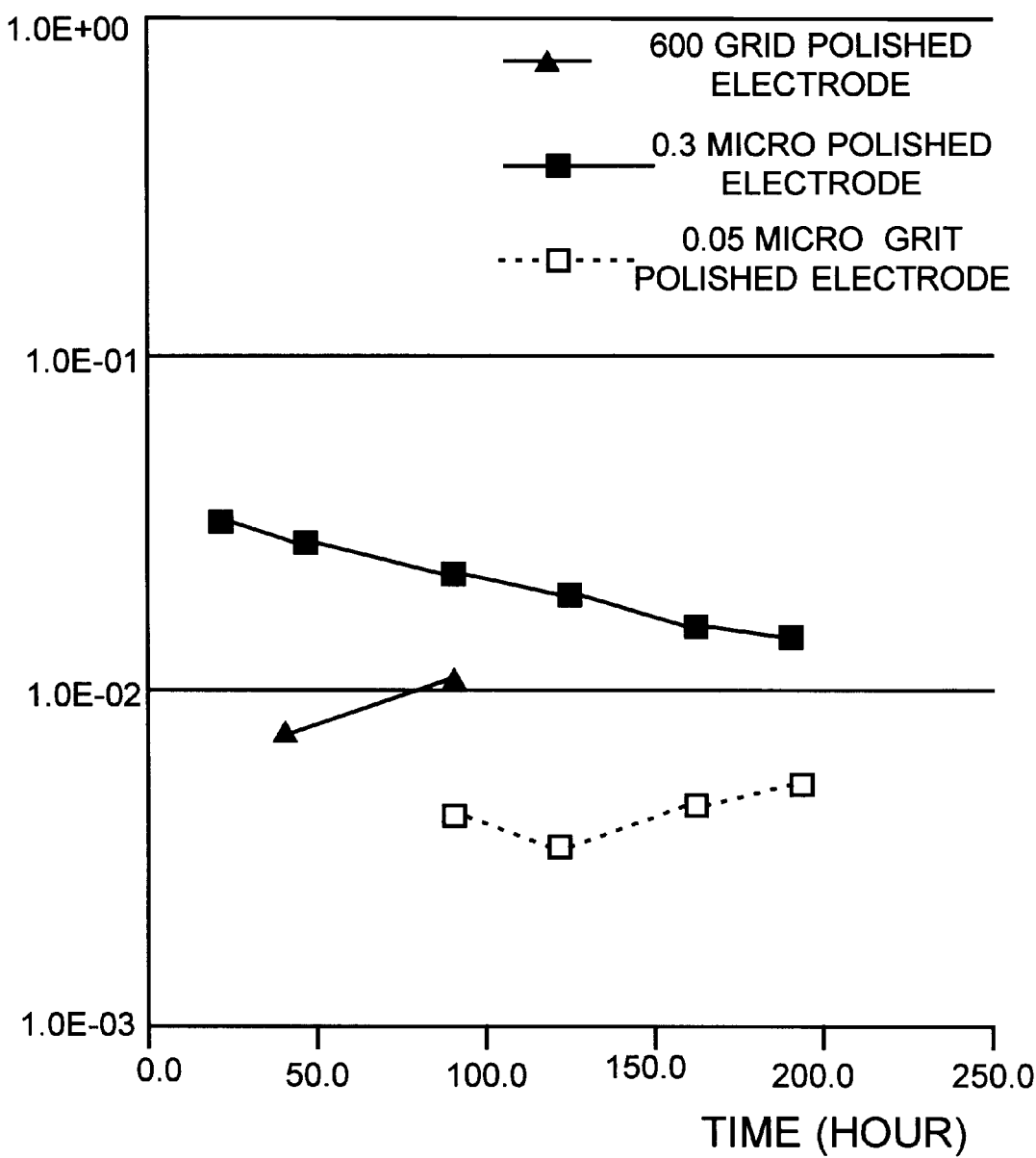

ELECTRODE DESIGN FOR CORROSION MONITORING USING ELECTROCHEMICAL NOISE MEASUREMENTS

CONTRACTUAL ORIGIN OF THE INVENTION

The United States Government has rights in this invention pursuant to Contract No. W-31-109-ENG-38 between the United States Government and Argonne National Laboratory.

FIELD OF THE INVENTION

The present invention relates to corrosion monitoring systems, and more particularly to, an improved electrode design for corrosion monitoring utilizing electrochemical noise measurements.

DESCRIPTION OF THE PRIOR ART

Metal corrosion is a major and costly problem for many industries. Two basic kinds of corrosion can be identified. General corrosion occurs uniformly over the entire surface of a metal structure and the rate of this form of corrosion can be easily monitored and predicted. Localized corrosion, however, is a more serious form of corrosion where rapid and sustained localized metal pitting occurs. This localized pitting corrosion can lead to the premature and catastrophic failure of metal pipes and storage vessels. The localized pitting corrosion can shorten the material life by orders of magnitude as compared to general corrosion or uniform corrosion. Early detection of localized pitting corrosion would result in cost savings because metal parts could be treated, repaired or replaced only when necessary thus avoiding unscheduled failures.

For years, engineers have been trying to develop effective monitoring methods to detect localized pitting corrosion. Among the innovative methods that were evaluated, electrochemical noise analysis (ENA) is recognized as one of the potential monitoring techniques. For example, U.S. Pat. No. 4,575,678 issued Mar. 11, 1986 discloses corrosion monitoring apparatus and corrosion monitoring method utilizing electrochemical noise analysis.

Electrochemical noise analysis is a non-destructive, in-situ monitoring method of the natural corrosion process that measures the electrochemical corrosion current and potential fluctuations. However, due to the chaotic nature of the corrosion process, signal processing of the recorded current and potential noise becomes very critical in determining the meaning of the recorded data.

Researchers have been interpreting the electrochemical noise analysis data by using different signal processing algorithms to quantitatively or qualitatively characterize the corrosion process. In an effort to specify the corrosion mechanisms and distinguish between uniform and localized pitting corrosion, they have monitored the signals for potential and current noise levels, noise resistance and pitting index (i.e., standard deviation of current noise divided by average current noise). Attempts have also been made to increase the sensitivity of the electrodes by applying an anodic bias voltage to the electrodes to accentuate localized corrosion as in U.S. Pat. No. 6,015,484. However, it was found that these results alone do not effectively identify the different corrosion mechanisms.

U.S. Pat. No. 5,888,374 issued to Daniel H. Pope, YuPo J. Lin, Edward J. St. Martin, and James R. Frank, on Mar. 30, 1999 and assigned to the present assignee disclosed an improved method and apparatus for monitoring localized pitting corrosion in metal pipes or storage vessels. The electrochemical probes include a pair of working electrodes formed of the same material as the monitored metal pipes or storage vessels and a reference electrode formed of a corrosion resistant material. Electrochemical probes are used for sensing electrochemical noise voltage and current values. The root-mean-square of the electrochemical voltage values are calculated and stored as the sensed electrochemical noise voltage level. The stored electrochemical noise voltage level values are processed by transforming the stored electrochemical noise voltage level values into power spectral density data utilizing a fast Fourier transform. A slope of the power spectral density data relative to frequency is calculated. A linear slope of a low-frequency portion of the power spectral density data is calculated by using a least-square method.

A principal object of the present invention is to provide an improved electrode design for corrosion monitoring utilizing electrochemical noise measurements.

It is another object of the present invention to provide such an improved electrode design for monitoring corrosion in metal pipes or storage vessels that utilizes electrochemical noise analysis.

It is another object of the present invention to provide such an improved electrode design for monitoring corrosion in metal pipes or storage vessels that utilizes electrochemical noise data obtained with a plurality of electrochemical probes including a generally non-corroding reference electrode and a pair of working electrodes formed of the same material as the monitored metal pipes or storage vessels.

It is another object of the present invention to provide such an improved electrode design for monitoring corrosion in metal pipes or storage vessels that utilizes electrochemical noise data obtained with a plurality of electrochemical probes including a reference electrode and a pair of working electrodes, each having a defined surface roughness.

It is another object of the present invention to provide a method to increase the probability that sustained localized pitting corrosion will occur on the more polished surface of the electrodes used for monitoring corrosion in metal pipes or storage vessels and be detected by analyzing voltage noise data obtained from electrochemical noise measurements.

It is another object of the present invention to provide a reproducible and accurate measure of the general corrosion rate on the unpolished electrode by analyzing the current noise data obtained from the electrochemical noise measurements.

It is another object of the present invention to provide such an electrode design that overcomes many of the disadvantages of prior art arrangements. For instance, the sensitivity of an unpolished electrode to develop localized pitting corrosion is low and it is hard to correlate the general corrosion rate on a pair of working electrodes with the ECN measurements.

SUMMARY OF THE INVENTION

In brief, these and other objects and advantages of the invention are provided by an electrode design for corrosion monitoring using electrochemical noise measurements. Electrochemical probes are used for sensing electrochemical noise voltage values and electrochemical noise current values. The electrochemical probes include a pair of working electrodes and a reference electrode. Each of the pair of working electrodes has a defined surface roughness. One of the pair of working electrodes has reduced roughness, whereby sensitivity to sustained localized pitting corrosion is increased in the working electrode with the reduced roughness.

In accordance with features of the invention, one of the pair of working electrodes has a defined surface roughness prepared by surface polishing the surfaces by using different grits of polishing cloth and/or different particle sizes of polishing slurries. The electrode surfaces were polished by using either a 600 grit polishing cloth or polishing slurry with particle sizes in the range of 1.0 micrometer to 0.05 micrometer. Thus, by reducing the surface roughness of one of the working electrodes, increased sensitivity to sustained localized pitting corrosion is provided. Meanwhile, the unpolished electrode with a rougher surface has higher general corrosion attack than the smooth surface. Therefore, we have found that, by electrically connecting these electrodes, the unpolished electrode will serve as the anodic site (i.e., corrosion) and the polished electrode will serve as the cathodic site for the corrosion process. Thus, the net corrosion current measured by a zero-resistance amperometer can be accurately used to measure the general corrosion rate of the unpolished electrode.

BRIEF DESCRIPTION OF THE DRAWINGS

The present invention together with the above and other objects and advantages may best be understood from the following detailed description of the preferred embodiments of the invention illustrated in the drawings, wherein:

FIGS. 2, 3 and 4 are charts illustrating the ENA results using the improved electrode design measured from electrochemical noise monitoring system of FIG. 1.

DETAILED DESCRIPTION OF THE PREFERRED EMBODIMENTS

Sustained localized pitting corrosion is a very important problem in many industries. The improved electrode design of the invention is used for monitoring for local pitting corrosion and general corrosion in steel pipes or storage vessels. The pitting corrosion is generally due to microbial attack, which can be treated with biocides once detected. A probe containing three electrodes is placed in the area where pitting corrosion may be expected to occur. Electrochemical noise analysis (ENA) of the electrochemical noise created by the corrosion indicates the presence of pitting corrosion. The spectrum of the electrochemical potential noise is analyzed in the frequency domain by Fourier analysis to give a power spectral density (PSD). The slope of PSD versus frequency relates to the corrosion mechanism. Pitting corrosion is characterized by very low frequencies. The present invention provides improvements over the earlier monitoring arrangements through the use of the improved electrode design.

Figure 1:
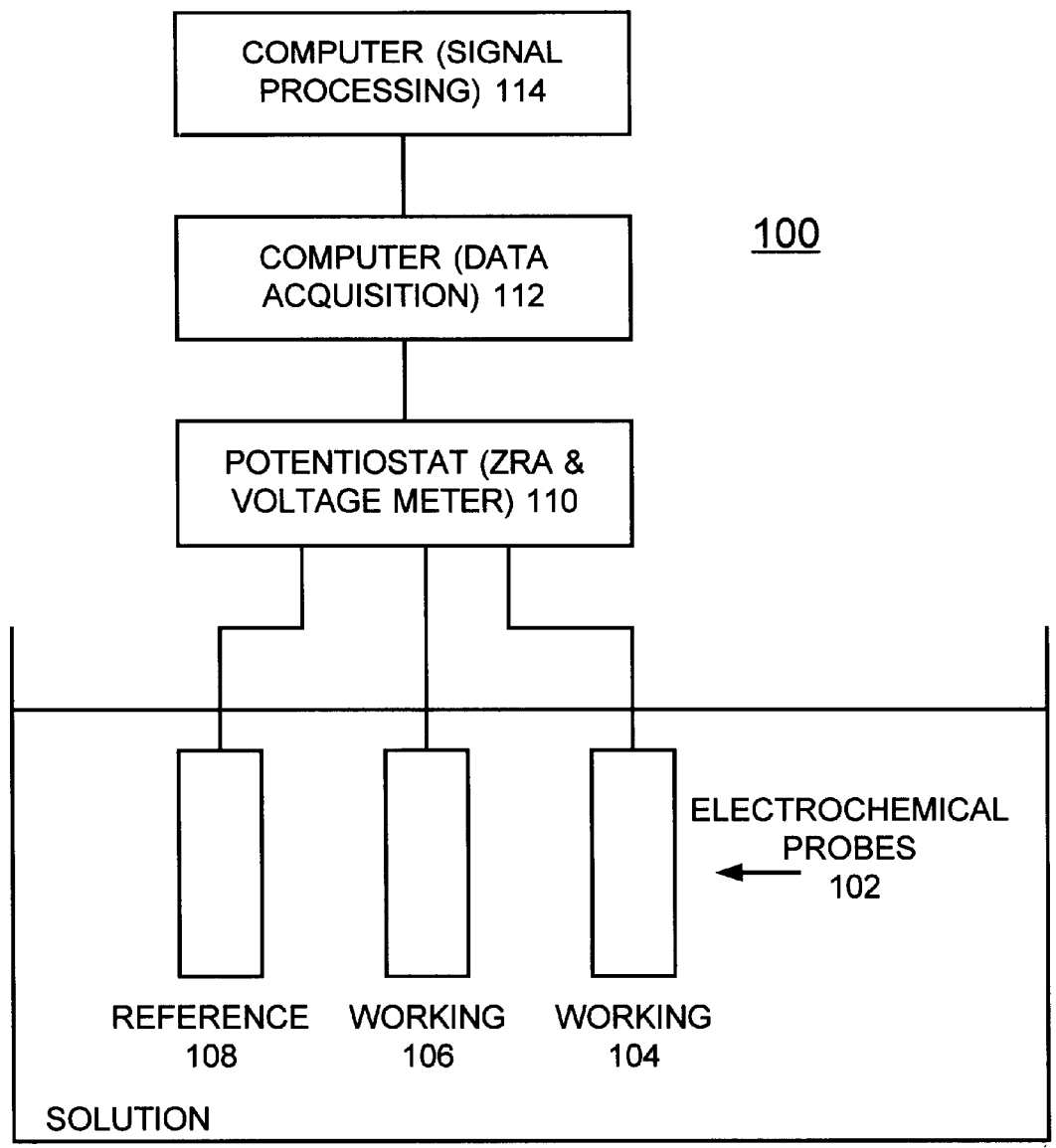
FIG. 1 is a schematic and block diagram representation of an electrochemical noise monitoring system in accordance with the present invention.

Having reference now to the drawings, in FIG. 1, there is shown an electrochemical noise monitoring system in accordance with the present invention generally designated by the reference character 100. Electrochemical noise (EN) monitoring system 100 includes an electrochemical noise probe 102 including a pair of working electrodes 104 and 106 and a reference electrode 108. A detected corrosion signal from a plurality of electrochemical probes 102 is applied to a potentiostat 110. The electrochemical probes 102 are connected to the potentiostat 110, which serves as a zero-resistant amperometer (ZRA) and a high impedance voltage meter. The signals recorded by the potentiostat 110 are stored in the computer by a computer data acquisition function 112. The acquired current noise data and acquired voltage noise data are processed using a signal processing function software 114 provided by the same computer of monitoring system 100. A data acquisition function and processing of the acquired current noise data and acquired voltage noise data using a signal processing function software are described in the above-identified U.S. Pat. No. 5,888,374 issued to Daniel H. Pope, YuPo J. Lin, Edward J. St. Martin, and James R. Frank, on Mar. 30, 1999 and assigned to the present assignee. The subject matter of the U.S. Pat. No. 5,888,374 is incorporated herein by reference.

The working electrodes 104 and 106 are shorted and connected through the zero-resistance amperometer (ZRA) 110. Current noise between the working electrodes was measured by the ZRA. The third electrode 108, called the reference electrode 108, is parallel connected with the other electrodes via the voltage meter 110. The working electrodes 104 and 106 are formed of the same material as the steel pipes or storage vessel to be monitored. The reference electrode 108 is formed of a non-corrosive or highly corrosion resistant material. Conventional or traditional electrochemical noise probes include three identical material electrodes or probes used to measure the electrochemical noise. The non-corroding or very corrosion resistant material used for the reference electrode 108 in the electrochemical noise monitoring system 100 substantially avoids interference by an otherwise corroding reference electrode observed in traditional three-probe electrochemical noise measurement devices.

The electrochemical noise detecting system 100 for pitting corrosion measurements includes three major components including a personal computer, such as an IBM or Dell personal computer performing the data acquisition function 110 and signal processing function 114. The potentiostat 110 and electrochemical probes 102 can be provided with a PC plug-in potentiostat/PC interface card, such as a PC-3 interface card manufactured and sold by Gamry Instruments, Inc. and the three-electrode electrochemical probes 104, 106 and 108, for example, manufactured and sold by Rohrback Cosasco, Inc.

In accordance with features of the invention, the surface morphology of the working electrodes 104, 106 is modified in the three-electrode electrochemical noise (EN) probe. By reducing the surface roughness of one, 104 or 106, of the pair of working electrodes 104, 106, increased sensitivity to sustained localized pitting corrosion is provided while the general corrosion rate of the unpolished electrode can be accurately measured by the average corrosion current obtained from the ECN measurements. By using one smooth working electrode 104 or 106, enhanced measurement of sustained localized pitting corrosion is provided and the other rough working electrode provides enhanced measurement of general or uniform corrosion. Reducing surface roughness of a metal will increase its general corrosion resistance. The reduction of metal surface roughness will therefore increase the tendency for localized corrosion attack. Thus, the corrosion potential advantageously is used to measure pitting corrosion attack on the smooth electrode while the average corrosion current is used to measure the general corrosion rate of the rough electrode. Each of the pair of working electrodes 104, 106, has a defined surface roughness prepared by different grits of polishing cloth (e.g., 600 grit) or polishing slurry solution with the particle size of the slurry in the range of 1.0 micrometer to 0.05 micrometer.

Figure 2:
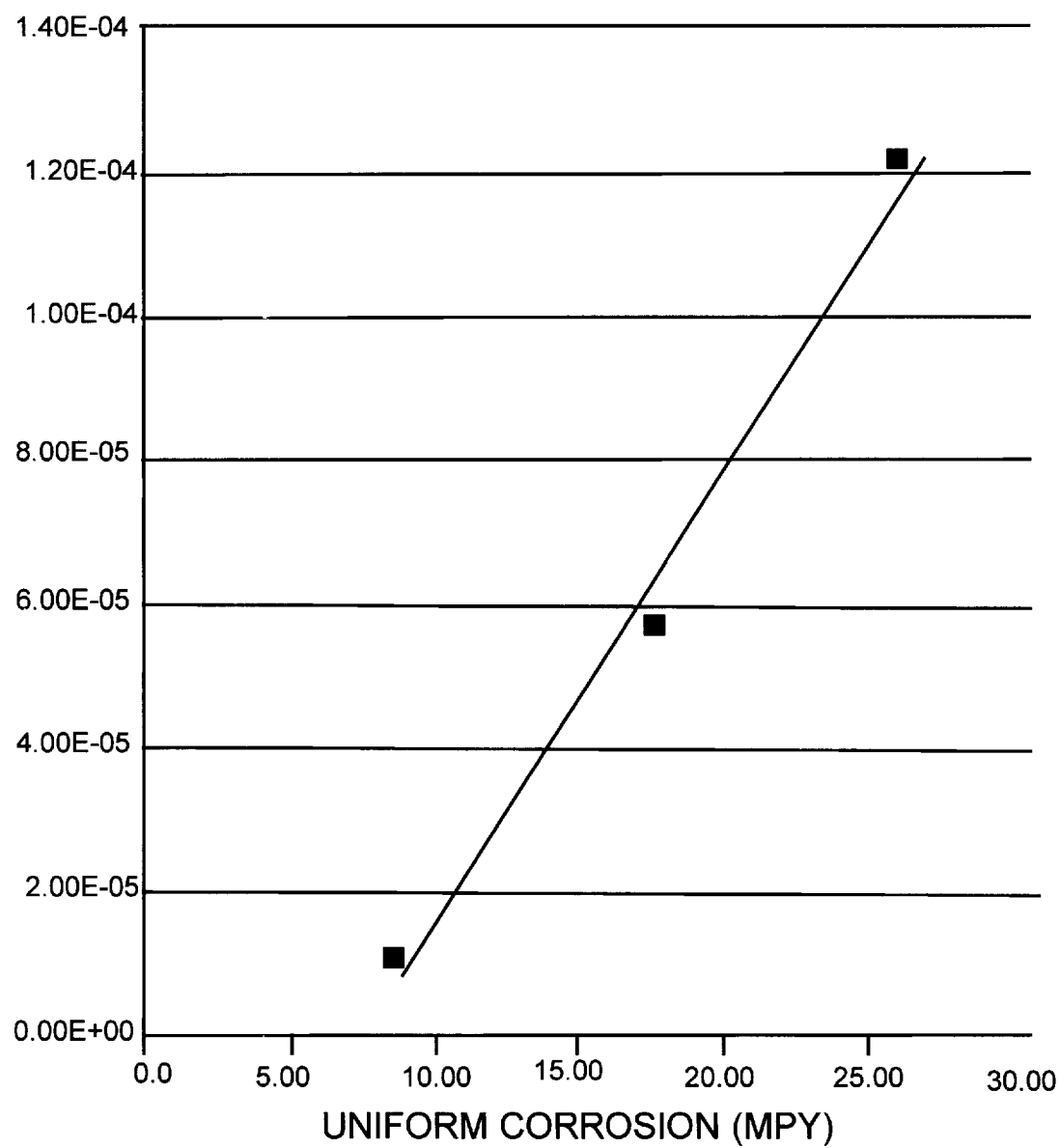
Figure 3:
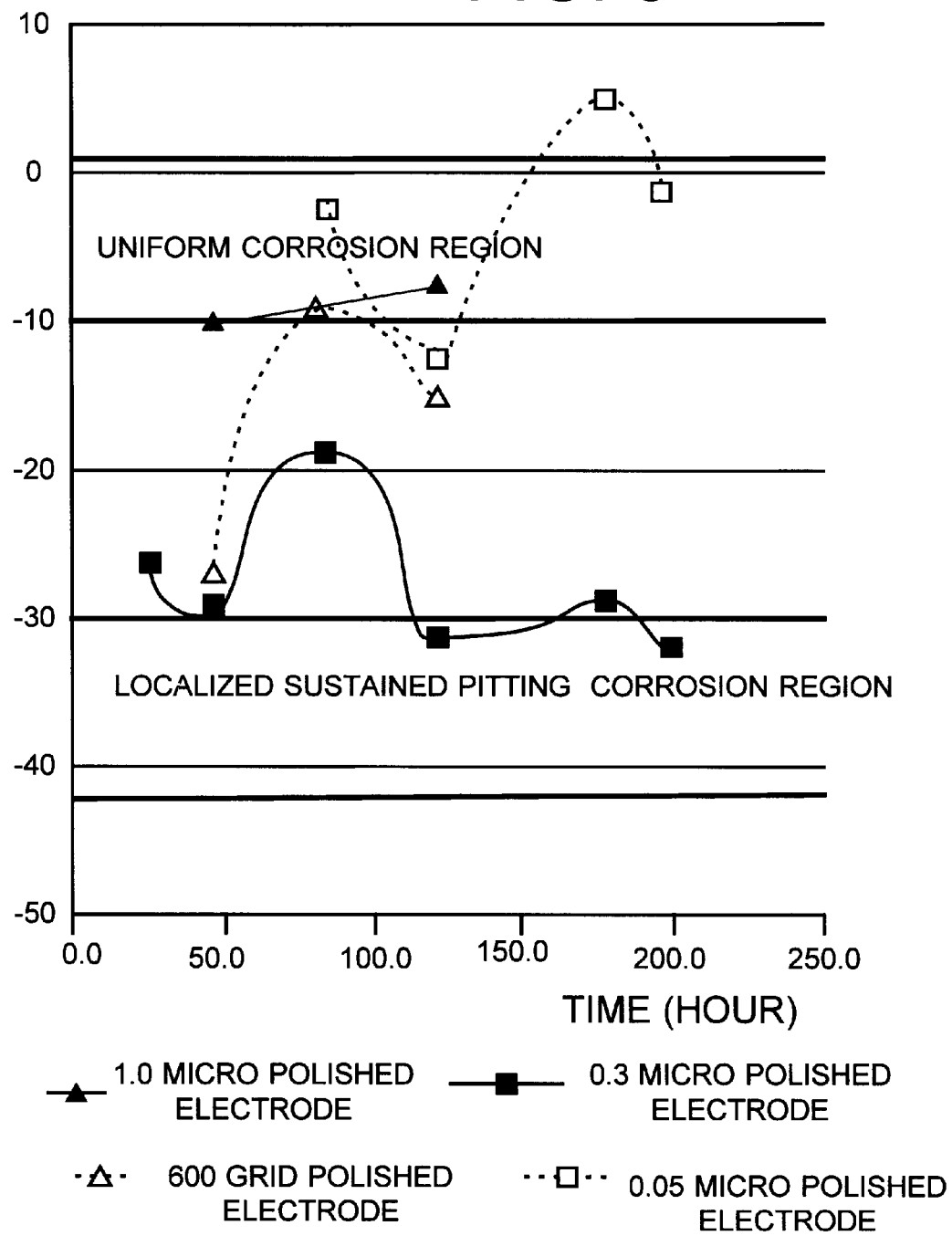

FIGS. 2, 3 and 4 illustrate electrochemical noise analysis results including the improved electrode design 102 including the new electrochemical probes 104 and 106 of invention in the electrochemical noise monitoring system 100 of FIG. 1. FIG. 2 illustrates correlation of average corrosion current measured by the zero-resistance amperometer and the uniform corrosion rate (measured by weight loss) and $R^2$ equals 0.9915. The average corrosion currents were calculated by the total ionic charges (i.e., the sum of the integration of current noise vs. time) due to the corrosion and divided by the total sampling time. In FIG. 3, the power spectral density of potential noise level (PSDPNL) is shown along the vertical axis. The transformed signal is called a power spectral density (PSD). The slope of the PSD versus frequency is related to pitting corrosion. Time in hours is shown along the horizontal axis in FIGS. 3 and 4. In FIG. 3, operation of four different probes with one working electrode polished with a 600 grit polishing cloth and 1.0, 0.3, and 0.05 micrometer particle sizes of polishing slurry solution are shown. In FIG. 4, average current index is shown along the vertical axis and operation of three different probes, each probe with one polished working are shown.

In Table 1, electrochemical noise as well as weight loss measurements were made with the initial and final weights shown in grams (g). Table 1 lists the preliminary results for corrosion experiment using carbon steel in NaCl solutions and the new electrode design 102. To verify the effect of metal surface roughness on the corrosion process, two experiments were carried out. From Table 1, it is clearly shown that the polished working electrodes appeared to have a much lower general corrosion rate than the unpolished working electrode. Inspection of the metal surface morphology also indicated that the reduced surface roughness could increase the tendency for localized sustained pitting corrosion attack. Therefore, the improved electrochemical noise probe 102 can be used to simultaneously measure the influences of the corrosion environment on general corrosion as well as localized sustained pitting corrosion of the monitored metal surfaces. The following Tables 2 and 3 provide additional test results.

TABLE 1

Results for the corrosion experiment using carbon steel in NaCl solutions and the new electrode design 102.

|  | Initial (g) | final (g) | time (hour) | General Corrosion (Rate Average) (MPY) | Corrosion Mechanism potential | Remark |
|---|---|---|---|---|---|---|
| ECN281W1 | 3.5621 | 3.5609 | 84.2 | 1.3 | Localized pitting | Polished |
| ECN281W2 | 3.5769 | 3.5703 | 84.2 | 7.2 | Uniform corrosion |  |
| ECN281R | 3.4263 | 3.4255 | 84.2 | 0.8 |  |  |
| ECN282W1 | 3.5893 | 3.5837 | 84.2 | 6.1 | Uniform corros'n |  |
| ECN282W2 | 3.5714 | 3.5592 | 84.2 | 2.4 | Localized pitting | Polished |
| ECN282R | 3.4189 | 3.4185 | 84.2 | 0.4 |  |  |

TABLE 2

|  | Initial (g) | final (g) | time (hour) | General Corrosion (Rate) (g/hour) | (MPY) | Corrosion Mechanism Average potential | Remark |
|---|---|---|---|---|---|---|---|
| ECN311W1 | 3.5652 | 3.5523 | 136.3 | 9.46E − 05 | 8.65 | Uniform | Mill |
| ECN311W2 | 3.5391 | 3.5285 | 136.3 | 7.78E − 05 | 7.10 | Uniform/LP | 600 grit |
| ECN311R | 3.5428 | 3.5405 | 136.3 | 1.61E − 05 | 1.47 | Uniform | mill |
| ECN312W1 | 3.5807 | 3.5684 | 136.3 | 9.02E − 05 | 8.24 | Uniform | Mill |
| ECN312W2 | 3.5208 | 3.5112 | 136.3 | 7.04E − 05 | 6.43 | LP | 1.0 μm |
| ECN312R | 3.5459 | 3.5435 | 136.3 | 1.76E − 05 | 1.61 | Uniform | mill |

TABLE 3

|  | Initial (g) | final (g) | time (hour) | General Corrosion (Rate) (g/hour) | (MPY) | Corrosion Mechanism Average potential | Remark |
|---|---|---|---|---|---|---|---|
| ECN321W1 | 3.605 | 3.5136 | 191.6 | 2.76E − 04 | 25.23 | Uniform | Mill |
| ECN321W2 | 3.5514 | 3.5414 | 191.6 | 5.22E − 05 | 7.10 | LP | 0.03 μm |
| ECN321R | 3.6443 | 3.6424 | 191.6 | 9.92E − 06 | 1.47 |  | mill |
| ECN322W1 | 3.5343 | 3.5136 | 191.6 | 1.08E − 04 | 8.24 | LP | 0.05 μm |
| ECN322W2 | 3.5883 | 3.5531 | 191.6 | 1.84E − 04 | 16.793 | Uniform | mill |
| ECN322R | 3.6308 | 3.6302 | 191.6 | 1.76E − 06 | 0.29 |  | mill |

What is claimed is:

1. An electrode design for monitoring corrosion in metal pipes or storage vessels comprising:

electrochemical probe means for sensing electrochemical noise, said electrochemical probes means including a pair of working electrodes and a reference electrode; and each of said pair of working electrodes having a defined surface roughness; one of said pair of working electrodes having reduced roughness, whereby sensitivity to sustained localized pitting corrosion is increased in the working electrode with said reduced roughness.

2. An electrode design for monitoring corrosion in metal pipes or storage vessels as recited in claim 1 wherein said electrochemical probe means includes said reference electrode formed of a corrosion resistant material.

3. An electrode design for monitoring corrosion in metal pipes or storage vessels as recited in claim 1 wherein said electrochemical probe means includes said pair of working electrodes formed of the same material of the monitored metal pipes or storage vessels.

4. An electrode design for monitoring corrosion in metal pipes or storage vessels as recited in claim 1 wherein said electrochemical probe means by reducing the surface roughness of one of said pair of working electrodes, increased sensitivity to sustained localized pitting corrosion is provided while also enabling the other electrode to accurately measure a general corrosion rate.

5. An electrode design for monitoring corrosion in metal pipes or storage vessels as recited in claim 1 wherein a general corrosion rate of the working electrode without surface polishing is accurately correlated with a measured noise current by the electrochemical noise technique.

6. An electrode design for monitoring corrosion in metal pipes or storage vessels as recited in claim 1 wherein said one of said pair of working electrodes having reduced roughness is polished with a 600 grit polishing cloth.

7. An electrode design for monitoring corrosion in metal pipes or storage vessels as recited in claim 1 wherein said one of said pair of working electrodes having reduced roughness is polished with a polishing slurry with particle sizes in the range of 1.0 micrometer to 0.05 micrometer.

8. An electrode design for monitoring corrosion in metal pipes or storage vessels comprising:

electrochemical probe means for sensing electrochemical noise, said electrochemical probes means including a pair of working electrodes formed of the same material of the monitored metal pipes or storage vessels and a reference electrode formed of a corrosion resistant material; and each of said pair of working electrodes having a defined surface roughness; one of said pair of working electrodes having reduced roughness, whereby sensitivity to sustained localized pitting corrosion is increased in the working electrode with reduced roughness.

9. A method for monitoring localized pitting corrosion in metal pipes or storage vessels comprising the steps of:

utilizing electrochemical probes and sensing electrochemical noise voltage values and electrochemical noise current values, providing said electrochemical probes with a pair of working electrodes and a reference electrode;

providing each of said pair of working electrodes with a defined surface roughness; and one of said pair of working electrodes having reduced roughness, whereby sensitivity to sustained localized pitting corrosion is increased in the working electrode with reduced roughness.

10. A method for monitoring localized pitting corrosion in metal pipes or storage vessels as recited in claim 9 wherein the step of providing each of said pair of working electrodes with a defined surface roughness; and one of said pair of working electrodes having reduced roughness includes the step of polishing said one of said pair of working electrodes having reduced roughness with a 600 grit polishing cloth.

11. A method for monitoring localized pitting corrosion in metal pipes or storage vessels as recited in claim 9 wherein the step of providing each of said pair of working electrodes with a defined surface roughness; and one of said pair of working electrodes having reduced roughness includes the step of polishing said one of said pair of working electrodes having reduced roughness with a polishing slurry with particle sizes in the range of 1.0 micrometer to 0.05 micrometer.

12. A method for monitoring localized pitting corrosion in metal pipes or storage vessels as recited in claim 9 includes the step of correlating a general corrosion rate from the working electrode without reduced surface roughness using a measured electrochemical noise current.

* * * * *